(12) United States Patent
Siegal et al.

(10) Patent No.: US 8,672,977 B2
(45) Date of Patent: Mar. 18, 2014

(54) DEVICE AND METHOD FOR SPINOUS PROCESS DISTRACTION

(75) Inventors: Tzony Siegal, Moshav Shoeva (IL); Yinnon Elisha, Tel Mond (IL)

(73) Assignee: NLT Spine Ltd., Kfar Saba (IL)

( * ) Notice: Subject to any disclaimer, the term of this patent is extended or adjusted under 35 U.S.C. 154(b) by 360 days.

(21) Appl. No.: 12/669,794

(22) PCT Filed: Aug. 11, 2008

(86) PCT No.: PCT/IB2008/053215
§ 371 (c)(1),
(2), (4) Date: Jan. 20, 2010

(87) PCT Pub. No.: WO2009/019669
PCT Pub. Date: Feb. 12, 2009

(65) Prior Publication Data
US 2010/0198263 A1  Aug. 5, 2010

Related U.S. Application Data

(60) Provisional application No. 60/954,825, filed on Aug. 9, 2007.

(51) Int. Cl.
*A61B 17/70* (2006.01)
(52) U.S. Cl.
USPC .......................................................... 606/249
(58) Field of Classification Search
USPC ..................... 606/247–249; 623/17.11–17.16
See application file for complete search history.

(56) References Cited

U.S. PATENT DOCUMENTS

| | | | | |
|---|---|---|---|---|
| 6,387,130 B1 * | 5/2002 | Stone et al. | ................ | 623/17.16 |
| 6,402,750 B1 * | 6/2002 | Atkinson et al. | .............. | 606/279 |
| 6,461,359 B1 * | 10/2002 | Tribus et al. | .................. | 606/247 |
| 7,959,652 B2 | 6/2011 | Zucherman et al. | | |
| 8,021,429 B2 * | 9/2011 | Viker | ......................... | 623/17.16 |
| 8,025,697 B2 * | 9/2011 | McClellan et al. | ........ | 623/17.11 |
| 8,034,110 B2 * | 10/2011 | Garner et al. | .............. | 623/17.11 |
| 8,105,365 B2 * | 1/2012 | Cragg | ........................... | 606/279 |
| 8,349,013 B2 | 1/2013 | Zucherman et al. | | |
| 2003/0187445 A1 * | 10/2003 | Keith et al. | ...................... | 606/72 |
| 2005/0261683 A1 * | 11/2005 | Veldhuizen et al. | ............ | 606/61 |
| 2006/0036273 A1 * | 2/2006 | Siegal | ............................ | 606/190 |
| 2006/0142858 A1 * | 6/2006 | Colleran et al. | ........... | 623/17.11 |
| 2006/0189999 A1 * | 8/2006 | Zwirkoski | ....................... | 606/90 |
| 2006/0265077 A1 * | 11/2006 | Zwirkoski | .................. | 623/17.16 |
| 2007/0067035 A1 * | 3/2007 | Falahee | ....................... | 623/17.11 |
| 2007/0260314 A1 * | 11/2007 | Biyani | ........................ | 623/17.11 |
| 2008/0125865 A1 * | 5/2008 | Abdelgany | ................. | 623/17.16 |
| 2008/0133012 A1 * | 6/2008 | McGuckin | ................. | 623/17.12 |

(Continued)

*Primary Examiner* — Mary Hoffman
(74) *Attorney, Agent, or Firm* — Mark M. Friedman

(57) ABSTRACT

An implant for maintaining a given minimum inter-spinous-process spacing includes an implant body with a number of segments hingedly interconnected so as to assume a straightened state for delivery along a conduit and a curved deployed state. An elongated tightening element is anchored at the distal segment of the implant body and passes along a channel extending along the implant body. Tension applied to the tightening element biases the implant body from the straightened state to the curved deployed state. Preferably, when the tightening element is deflected to reach the curved deployed state, a locking arrangement locks the tightening element relative to the implant body, thereby retaining the implant in the curved deployed state. A distal portion of the implant body is preferably formed with a set of lateral projections to inhibit withdrawal of the distal portion between adjacent spinous processes after deployment.

24 Claims, 8 Drawing Sheets

(56) References Cited

U.S. PATENT DOCUMENTS

| | | | |
|---|---|---|---|
| 2008/0208255 A1* | 8/2008 | Siegal | 606/246 |
| 2008/0221687 A1* | 9/2008 | Viker | 623/17.16 |
| 2008/0249628 A1* | 10/2008 | Altarac et al. | 623/17.16 |
| 2008/0312743 A1* | 12/2008 | Vila et al. | 623/17.16 |
| 2009/0005871 A1* | 1/2009 | White et al. | 623/17.11 |
| 2009/0240335 A1* | 9/2009 | Arcenio et al. | 623/17.16 |
| 2009/0254185 A1* | 10/2009 | Dollinger | 623/17.16 |
| 2009/0292323 A1* | 11/2009 | Chirico et al. | 606/86 R |
| 2012/0004731 A1* | 1/2012 | Viker | 623/17.16 |
| 2012/0071980 A1* | 3/2012 | Purcell et al. | 623/17.16 |

* cited by examiner

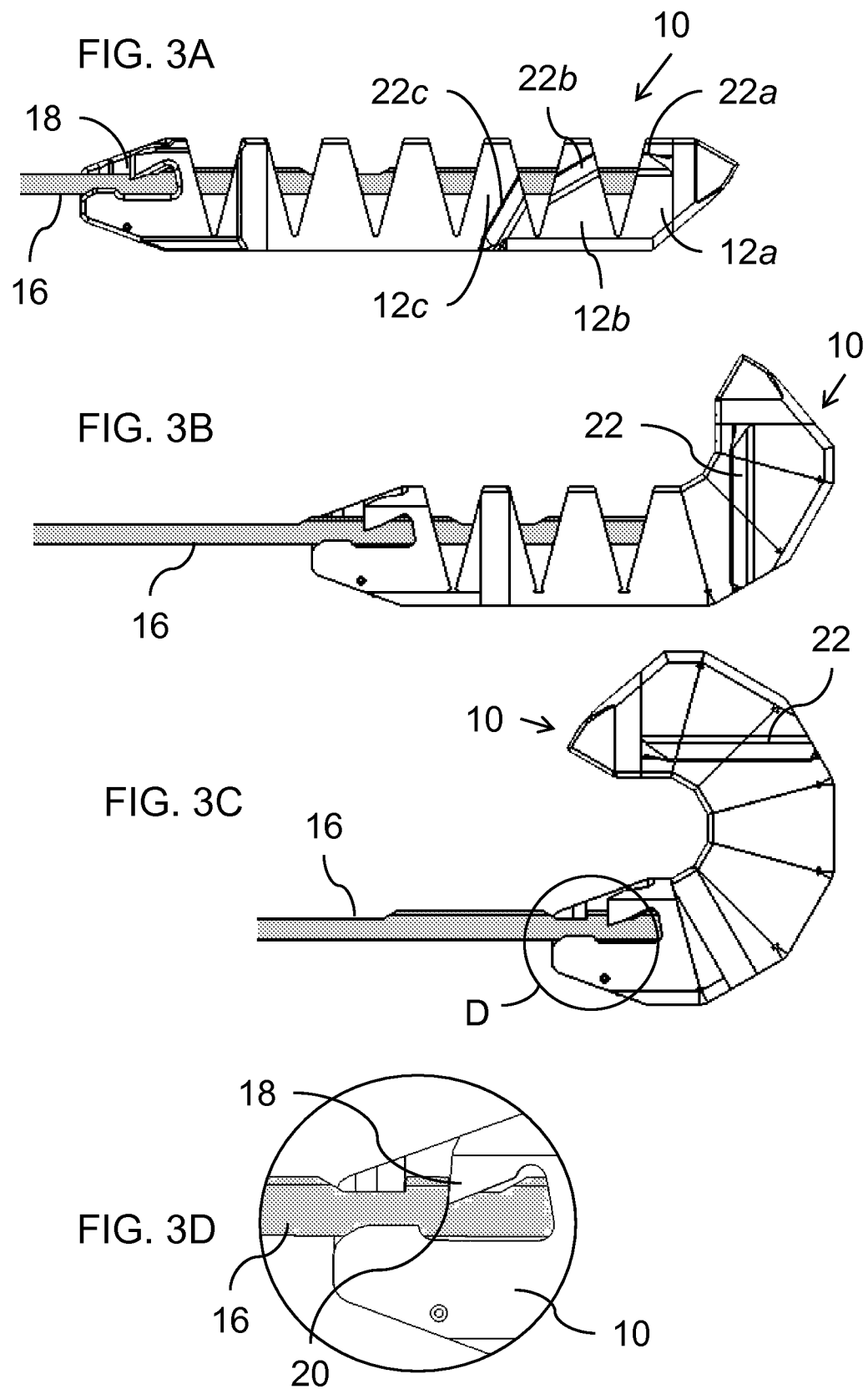

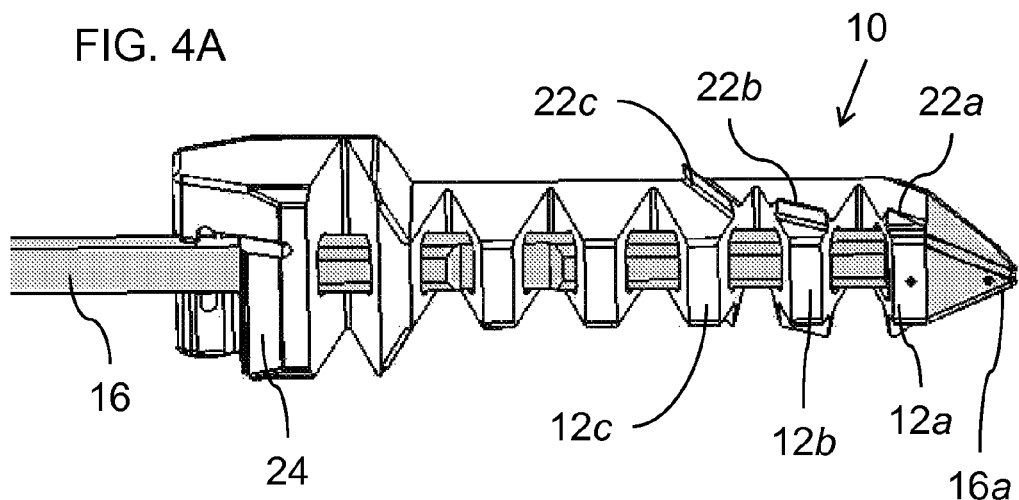
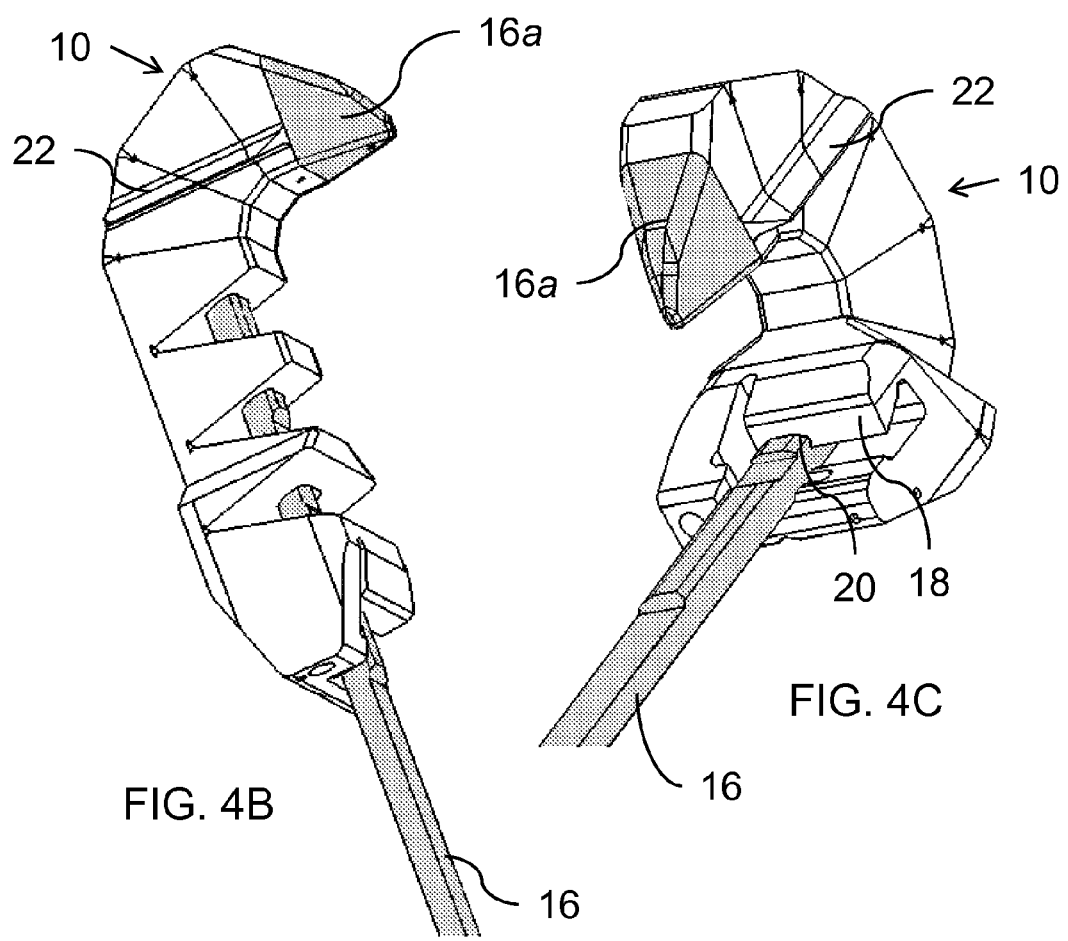

DEVICE AND METHOD FOR SPINOUS PROCESS DISTRACTION

RELATED APPLICATIONS

This patent application is a National Stage of PCT/IB2008/053215 filed on 11, Aug. 2008, which claims the benefit of U.S. Provisional Patent Application No. 60/954,825 filed Aug. 09, 2007, the contents of which are incorporated herein by reference.

FIELD AND BACKGROUND OF THE INVENTION

The present invention relates to spinous process distraction and, in particular, it concerns a device and method for minimally invasive deployment to achieve spinous process distraction.

Various devices have been proposed for distraction between adjacent spinous processes, or more precisely, to prevent extension at one or more level between adjacent vertebrae in order to treat various spinal conditions. Examples of such devices are described in U.S. Pat. Nos. 6,152,926, 6,695,842, US2004/0153071 and WO03007791 which may be referred to for further background to the physiological aspects of the present invention.

Although the above documents refer to minimally invasive techniques for implanting the devices disclosed, the deployment of the element in a latero-lateral direction via a dorsal-angled approach is non-trivial, requiring sizable incisions and manipulation within the body to achieve the required deployment of an implant. In some cases, spinous process distraction devices necessitate bilateral access during implantation, thereby necessarily increasing trauma from the procedure compared to a unilateral approach. On the other hand, attempts to implement a unilateral approach device would present more complex obstacles regarding the correct latero-lateral alignment of the device.

PCT patent application publication no. WO 2006/072941 teaches a wide range of devices and corresponding applications in which an elongated element is introduce into a body in a straightened configuration and then assumes a curved or coiled configuration within the body. The aforementioned publication is hereby incorporated by reference herein in its entirety.

It would therefore be highly advantageous to provide a method and device according to the principles of the aforementioned WO 2006/072941 which would employ the deflectable structure to facilitate correct placement of an inter spinous process implant from a unilateral dorsal-angled approach.

SUMMARY OF THE INVENTION

The present invention is an implant, a system for implantation, and a corresponding method, for maintaining a minimum inter-spinous-process spacing.

According to the teachings of the present invention there is provided, an implant for implantation between adjacent spinous processes of a human or animal subject for maintaining a given minimum inter-spinous-process spacing, the implant comprising: (a) an implant body including a plurality of segments hingedly interconnected so as to assume a straightened state for delivery along a conduit and a curved deployed state, the implant body having a channel passing from a distal one of the segments along a majority of a length of the body; and (b) an elongated tightening element anchored at the distal segment of the body and passing along the channel, the body and the tightening element being configured such that tension applied to the tightening element tends to bias the implant body from the straightened state to the curved deployed state, wherein the implant body and the tightening element are configured to provide a locking arrangement such that, when the tightening element is deflected to reach the curved deployed state, the locking arrangement is effective to lock the tightening element relative to the implant body, thereby retaining the implant in the curved deployed state.

According to a further feature of the present invention, the implant body is formed with at least one resilient tooth, and wherein the tightening element is formed with at least one corresponding step, the resilient tooth and the corresponding step together providing the locking arrangement.

According to a further feature of the present invention, the curved deployed form exhibits a substantially U-shaped form.

According to a further feature of the present invention, a distal portion of the implant body is formed with a set of lateral projections configured for inhibiting withdrawal of the distal portion between adjacent spinous processes after deployment.

According to a further feature of the present invention, the lateral projections provide barbed ridges shaped to inhibit withdrawal of the distal portion between adjacent spinous processes after deployment.

According to a further feature of the present invention, the set of lateral projections includes projections from a plurality of the segments of the implant body, the projections being spaced apart when the implant body is in the straightened state and being juxtaposed when the implant is in the curved deployed state such that the projections cooperate to form at least one elongated retention feature extending along at least part of at least two of the segments.

According to a further feature of the present invention, the at least one elongated retention feature is a projecting ridge extending substantially perpendicular to a line joining a proximal and a distal end of the implant body.

According to a further feature of the present invention, the at least one elongated retention feature is a barbed ridge shaped to inhibit withdrawal of the distal portion between adjacent spinous processes after deployment.

According to a further feature of the present invention, the at least one elongated retention feature extends along at least part of at least three of the segments.

According to a further feature of the present invention, the implant body further includes a medial portion having a first width and a proximal block having a second width greater than the first width.

According to a further feature of the present invention, the implant body is formed primarily from a biocompatible polymer, and most preferably from ultra-high-molecular-weight poly-ethylene.

According to a further feature of the present invention, the tightening element is formed primarily from ultra-high-molecular-weight poly-ethylene.

There is also provided according to the teachings of the present invention, an implant system comprising: (a) the aforementioned implant; and (b) a delivery system including: (i) a conduit sized to receive the implant and to maintain the implant body in the straightened state, (ii) a pusher deployable at least partially within the conduit to advance the implant so as to emerge from a distal opening of the conduit, and (iii) a biasing arrangement associated with the tightening element and deployed to urge the tightening element rearward such that, as the implant emerges from the distal end of the conduit, the implant body is progressively deflected towards the curved deployed state.

According to a further feature of the present invention, the delivery system further includes a cutting mechanism selectively deployable to sever an excess length of the tightening element after locking of the locking arrangement.

There is also provided according to the teachings of the present invention, an implant for implantation between adjacent spinous processes of a human or animal subject for maintaining a given minimum inter-spinous-process spacing, the implant comprising: (a) an implant body including a plurality of segments hingedly interconnected so as to assume a straightened state for delivery along a conduit and a curved deployed state, the implant body having a channel passing from a distal one of the segments along a majority of a length of the body; and (b) an elongated tightening element anchored at the distal segment of the body and passing along the channel, the body and the tightening element being configured such that tension applied to the tightening element tends to bias the implant body from the straightened state to the curved deployed state, wherein a distal portion of the implant body is formed with a set of lateral projections configured for inhibiting withdrawal of the distal portion between adjacent spinous processes after deployment.

There is also provided according to the teachings of the present invention, a method for deployment of a spinous process spacer between spinous processes of a human or animal, the method comprising the steps of: (a) positioning a delivery conduit for dorsal minimally invasive approach to the inter-spinous-process space; (b) deploying within the delivery conduit an implant body including a plurality of segments hingedly interconnected so as to assume a straightened state while restrained within the delivery conduit, and being biased to assume a curved deployed state; and (c) advancing the implant body beyond a distal opening of the delivery conduit such that the implant body is progressively deflected to the curved deployed state, thereby following a curved deployment path passing laterally through the inter-spinous-process space.

BRIEF DESCRIPTION OF THE DRAWINGS

The invention is herein described, by way of example only, with reference to the accompanying drawings, wherein:

FIGS. 3A-3C are schematic side views of the implant of FIG. 2 in a straightened state prior to deployment, at an intermediate state during deployment, and in a curved deployed state, respectively;

FIG. 3D is an enlarged view of the region of FIG. 3C denoted by circle D showing a locking arrangement of the implant;

FIGS. 4A-4C are isometric view of the implant of FIG. 2 in states corresponding to FIGS. 3A-3C, respectively;

DESCRIPTION OF THE PREFERRED EMBODIMENTS

Figure 1A:
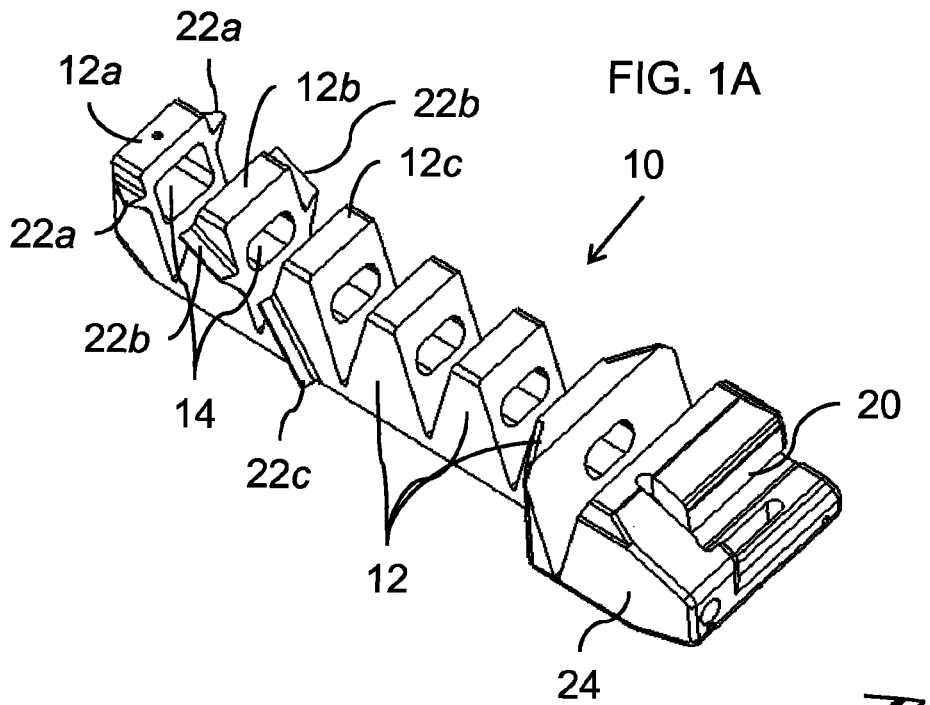
FIG. 1A is an isometric view of an implant body for use in an implant, constructed and operative according to the teachings of the present invention, for maintaining a minimum inter-spinous-process spacing.
Figure 1B:
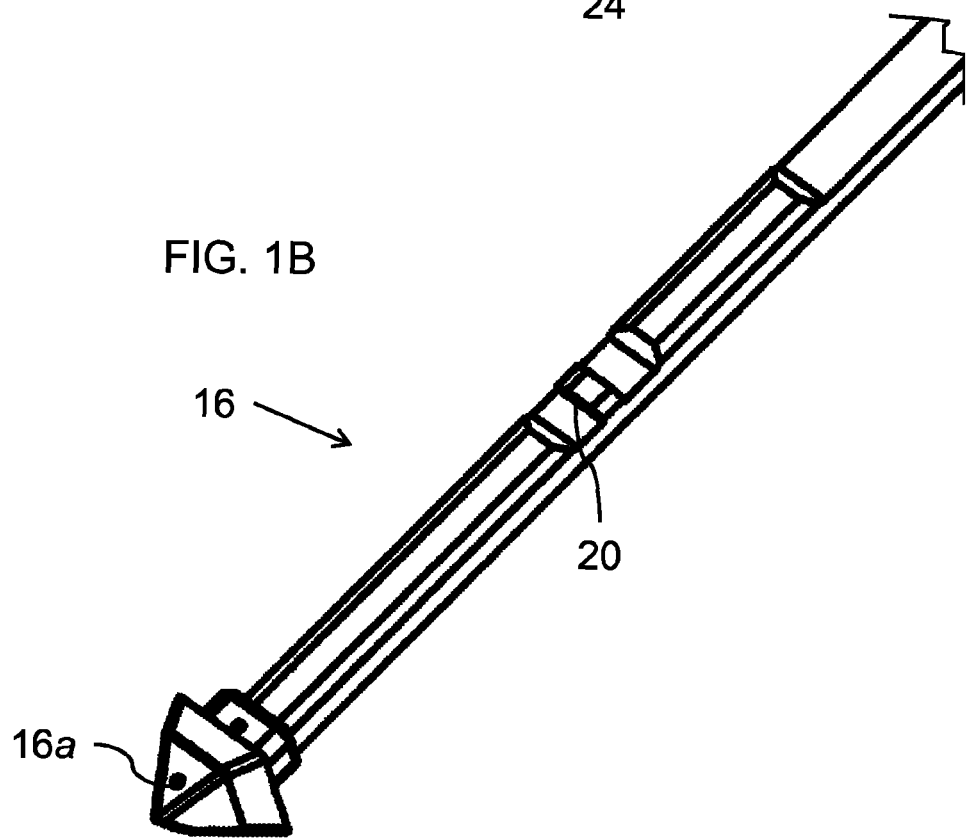
FIG. 1B is a partial isometric view of an elongated tightening element for use in an implant, constructed and operative according to the teachings of the present invention, for maintaining a minimum inter-spinous-process spacing.

The present invention is an implant, a system for implantation, and a corresponding method, for maintaining a minimum inter-spinous-process spacing.

The principles and operation of implants, systems and methods according to the present invention may be better understood with reference to the drawings and the accompanying description.

Referring now to the drawings, FIGS. 1A-7B show various parts of an implant, a corresponding delivery system, and the corresponding manner of deployment of the implant, constructed and operative according to the teachings of the present invention, for maintaining a given minimum inter-spinous-process spacing between adjacent spinous processes of a human or animal subject.

Figure 2:
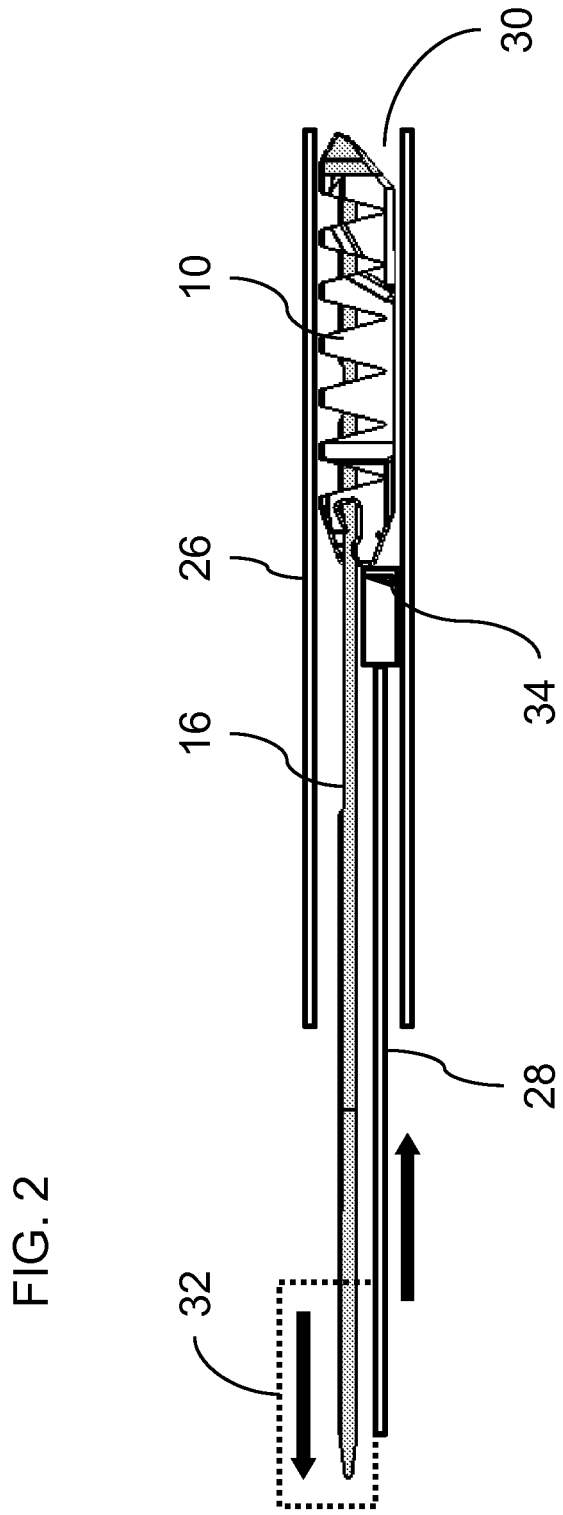
FIG. 2 is a schematic side cross-sectional view of an implant system, constructed and operative according to the teachings of the present invention, including an implant formed from the implant body of FIG. 1A and the tightening element of FIG. 1B, together with a delivery system.
Figure 5:
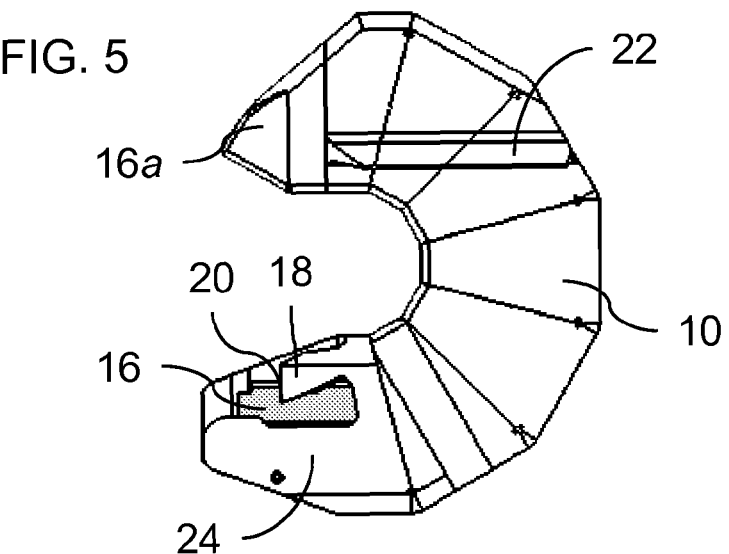
FIG. 5 is a side isometric view illustrating the implant of FIG. 2 in its curved deployed state after severing of an excess length of said tightening element.
Figure 6:
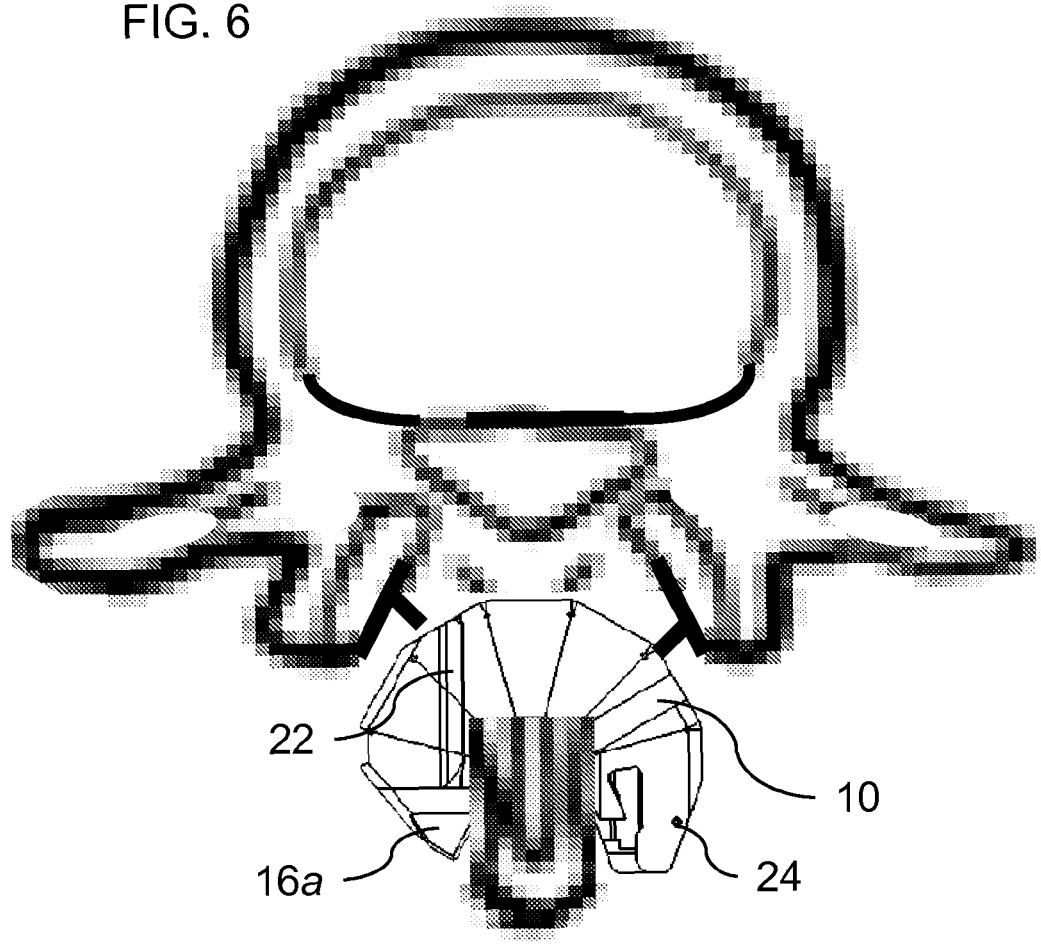
FIG. 6 is schematic superior view illustrating the position of the deployed implant relative to the inferior vertebra.
Figure 7A:
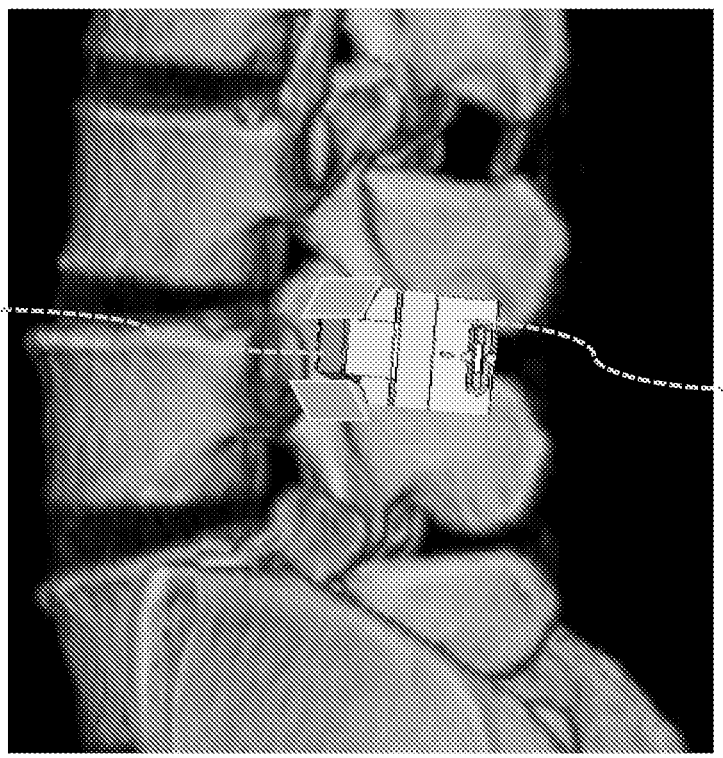
FIGS. 7A and 7B are schematic left and right lateral views, respectively, showing the position of the deployed implant relative to the vertebrae.
Figure 7B:
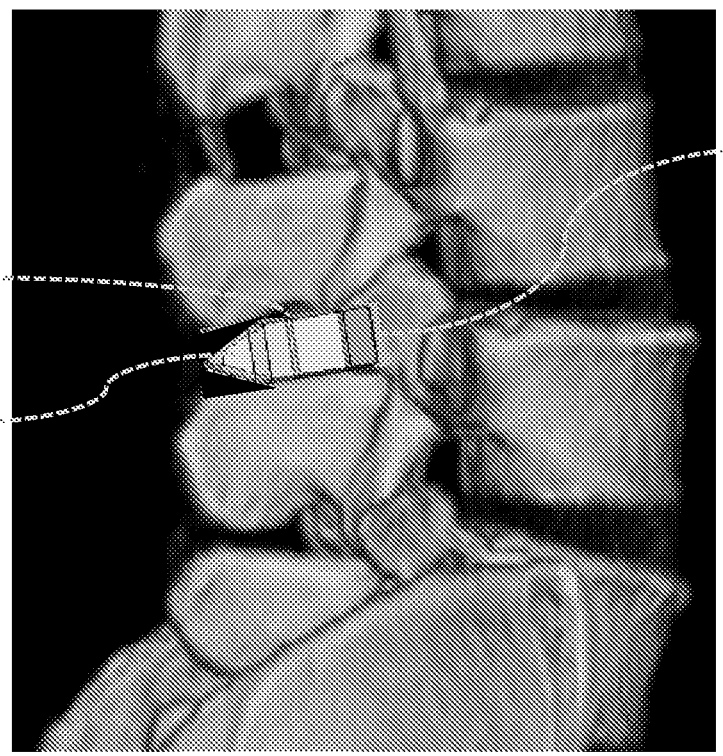

Generally speaking, the implant is formed from an implant body 10 including a plurality of segments 12 hingedly interconnected so as to assume a straightened state (FIGS. 2, 3A and 4A) for delivery along a conduit and a curved deployed state (FIGS. 3C, 4C and 5). A channel 14 passes from a distal segment 12a along a majority of a length of implant body 12. An elongated tightening element 16 is anchored at distal segment 12a and extends along channel 14, as best seen in FIG. 2. Implant body 10 and tightening element 16 are configured such that tension applied to the tightening element tends to bias the implant body from the straightened state to the curved deployed state.

According to one particularly preferred set of features, implant body 10 and tightening element 16 are configured to provide a locking arrangement such that, when tightening element 16 is withdrawn relative to implant body 10 so as to deflect implant body 10 to its curved deployed state, the locking arrangement is effective to lock tightening element 16 relative to implant body 10, thereby retaining the implant in the curved deployed state. One preferred implementation of the locking mechanism is best seen in FIG. 3D where implant body 10 is formed with at least one resilient tooth 18, and tightening element 16 is formed with at least one corresponding step 20. Resilient tooth 18 and corresponding step 20 are positioned so as to engage each other in the curved deployed configuration, thereby providing the required locking function.

According to another additional, or alternative, particularly preferred set of features, a distal portion of the implant body (e.g., segments 12a-12c) is formed with a set of lateral projections 22*a*, 22*b*, 22*c* configured for inhibiting withdrawal of the distal portion between adjacent spinous processes after deployment.

At this stage, it will already be apparent that the present invention and its various preferred features provide particular advantages over conventional inter-spinous-process spacers. Specifically, the transition of the implant body from the straightened state to the curved deployed state allows correct latero-lateral deployment of the implant using a unilateral minimally invasive dorsal approach and without requiring traumatic manipulation using gripping tools at the insertion site itself. Similarly, the use of lateral projections to form a retention configuration for the distal portion of the insert provides a particularly simple structure for achieving effective retention after unilateral insertion of the implant. These and other advantages of the present invention will become clearer in view of the following detailed description.

At this stage, it will be helpful to define certain terminology as used herein in the description and claims. Firstly, when referring to the implant of the present invention, the term "distal" is used to refer to the leading portion deployed first from the delivery system while "proximal" is used to refer to the portion deployed last. "Medial" refers to the intermediate portion.

The term "medial portion" typically refers to the portion which lies between the spinous processes when deployed, thereby providing the desired spacer effect. The dimension of the implant presented between the spinous processes is termed the "width" of the implant, and corresponds to the dimension perpendicular to the plane of curvature. The dimension of the segments radially relative to the center of curvature is termed "height", and the dimension along the path of insertion is termed "length". The direction of insertion is termed "forward" and the reverse direction is termed "rearward".

Turning now to the frame of reference of the body of the subject, all standard medical terminology is used in its normative sense unless explicit otherwise. Thus, the term "lateral" or "latero-lateral" refers to a direction from side-to-side in the body, i.e., lying roughly in a coronal plane. A "dorsal" approach refers to an approach for minimally invasive surgical access to the spinal region in which a stab incision is made adjacent to the spinous processes and a delivery conduit is inserted roughly perpendicular (e.g., within about 15 degrees of perpendicular) to a coronal plane. A "unilateral" approach refers to a procedure in which an incision is made only on one side of the spinal column.

Regarding the straightened state of implant body 10, it should be noted that this need not be precisely straight, but is rather "straightened" relative to the curved deployed state. It will be clear to one ordinarily skilled in the art that a gentle curvature of the delivery system conduit, and a corresponding initial gentle curvature to implant body 10, would not significantly impact the functionality of the invention as described.

The implant of the present invention is referred to as being "progressively deflected" as it is deployed from the delivery system. This refers to the preferred implementation in which tightening element 16 is rearwardly biased relative to implant body 10 such that each successive segment of implant body reaching the distal opening of the delivery system is deflected to its curved deployed state, while the segments remaining within the straight portion of the delivery system are still restrained to their substantially straightened state. The resulting partially deflected states are illustrated in FIGS. 3B and 4B, with the conduit removed.

The curved deployed state of implant body 10 is preferably a substantially fully deflected state, i.e., where the hinged interconnection between each pair of adjacent segments 12 has flexed to its limit of motion in one direction as defined by additional contact surfaces between the segments.

Turning now to the features of the present invention in more detail, implant body 10 may be implemented from a wide range of biocompatible materials. Examples include, but are not limited to, various biocompatible metals and metal alloys, and various biocompatible polymers. In one particularly preferred implementation, implant body is made primarily, and typically exclusively, from ultra-high-molecular-weight poly-ethylene (UHMWPE). UHMWPE provides a highly advantageous combination of low-friction, wear-resistance and resilience which is particularly suited to this application. In this case, tightening element 16 is most preferably also formed primarily from UHMWPE. In an alternative implementation also considered to be of significance, PEEK may be used as the primary or exclusive material for one or both of implant body 10 and tightening element 16.

Implant body 10 may be implemented with a wide range of cross-sectional shapes. In the example illustrated here, the implant is formed with a generally rectangular cross-section. Another particular preferred cross-sectional shape is a more rounded form, possibly approximating to an ellipse. In each case, the width of the medial portion of implant body defines the required minimum spacing between the spinous processes. Accordingly, a surgical kit for implementing the present invention preferably includes a plurality of implants, or at least a plurality of implant bodies 10, with differing widths between which the practitioner can choose according to the surgical needs. The heights of all the different width implants are preferably the same so that the same delivery system can be used for each.

Structurally, the effective hinges between segments 12 may be implemented in a wide range of ways. Most preferably, the hinged interconnection is achieved by integral hinges integrally formed with segments 12 either during an injection or molding process, or through cutting out of slots from an initial block of material. The slots may be V-shape, parallel sided, or any other suitable form. Most preferably, V-shaped slots are used so that the curved deployed form of the implant has the spaces between the segments essentially closed. However, alternative implementations, such as where the hinged interconnection is provided by a separate structure (e.g., a "backbone") to which segments 12 are attached, also fall within the scope of the present invention. In the latter case, the backbone may be of a different material from the segments themselves, chosen according to the intended application. Options for materials for the backbone include, but are not limited to, metallic materials, various plastics and other polymers, and fabrics.

The curved deployed form of implant body 10 is preferably a roughly arcuate form, typically extending around about 180 degrees to form what appears as a substantially "U-shaped" form. The term "U-shaped" is used herein to refer generically to any shape which has a medial portion which turns through roughly 180 degrees (i.e., 180 degrees plus or minus 20 degrees) without specifying in detail the shape, geometry or extent of the two side portions. (It is noted parenthetically that the letter "u" itself is asymmetric in many typefaces.)

A preferred implementation of the locking arrangement is best seen in FIGS. 3D and 4C. Resilient tooth 18 is preferably implemented as an integral part of a proximal block of implant body 10. The structure and dimensions of tooth 18 are chosen according to the mechanical properties of the materials used to provide sufficient resilience and secure locking. The corresponding step 20 may be implemented as any suitably positioned step, formed either by an upward projection or a recessed notch, or a combination thereof. Clearly, alternative locking arrangements employing different forms of engagement may also be used.

Turning now to lateral projections 22a, 22b and 22c, these are preferably implemented as a set of lateral projections including projections from at least two, and preferably three, segments 12 of implant body 10. These projections are spaced apart when implant body 10 is in its straightened state and are juxtaposed when implant 10 is in its curved deployed state such that the projections cooperate to form at least one elongated retention feature, designated collectively as 22, extending along at least part of the corresponding two or three segments. Retention feature 22 preferably provides a "barbed ridge", i.e., that has a directional structure with a steep step presented so as to inhibit withdrawal of the distal portion of implant body 10 between adjacent spinous processes after deployment. Most preferably, elongated retention feature 22 extends substantially perpendicular to a line joining a proximal and a distal end of implant body 10, such that it extends in a generally anterior-posterior direction parallel to the length of the spinous processes when deployed. The lateral projections are preferably provided symmetrically on both sides of the distal segments 12a-12c.

Implant body 10 preferably also features a proximal block 24 having a width greater than that of the medial portion. This provides retention of the implant in use to prevent the proximal portion of implant body 10 from advancing too far, thereby maintaining proper positioning of the implant with the medial portion between the spinous processes, retention feature 22 on one side and proximal block 24 on the other.

Referring now again to FIG. 2, this shows the implant of the present invention deployed within a delivery system. Specifically, the delivery system includes a conduit 26 sized to receive the implant and to maintain the implant body in the straightened state, a pusher 28 deployable at least partially within conduit 26 to advance the implant so as to emerge from a distal opening 30 of the conduit, and a biasing arrangement 32 deployed to urge tightening element 16 rearward. As a result, as the implant emerges from the distal end of the conduit, the implant body is progressively deflected towards the curved deployed state.

The delivery system is shown here only schematically. It will be appreciated that a practical implementation of the delivery system may take many forms. For example, pusher 28 may be a simple manual pusher as illustrated, or may include various manual or power-driven advancing mechanisms to move the implant forward in a convenient and controlled manner. Similarly, biasing arrangement 32 is shown schematically as a functional block, but may be implemented in various ways using arrangements of one or more springs or other biasing arrangements, all as will be clear to one ordinarily skilled in the art.

Most preferably, the delivery system also includes a cutting mechanism 34 selectively deployable to sever an excess length of tightening element 16 after the locking arrangement has been locked. In the schematic representation illustrated here, cutting mechanism 34 is illustrated as a blade associated with pusher 28 and actuated by rotating the pusher rod. Clearly, alternative implementations, possibly integrated with block 24 or conduit 26, are well within the capabilities of one ordinarily skilled in the art. The severing of tightening element 16 leaves the deployed implant in a free-standing configuration as illustrated in FIG. 5.

Turning now to the operation of the present invention, corresponding to a method according to the present invention for deployment of a spinous process spacer between spinous processes of a human or animal. Generally speaking, the method begins by positioning delivery conduit 26 through a minimally invasive incision, typically of roughly 2 cm length, in a dorsal approach to the inter-spinous-process space. The conduit is preferably deployed within 20 degrees to the perpendicular to a coronal plane, and most preferably directly perpendicular.

Implant body 10 is then advanced beyond distal opening 30 of delivery conduit 26 so that implant body 10 is progressively deflected to the curved deployed state, thereby following a curved deployment path passing laterally through the inter-spinous-process space. This leads to the deployment position depicted schematically in FIGS. 6, 7A and 7B.

Where necessary, if the implant is not used to open its own path through the inter-spinous-process tissue, a suitable tool for penetrating the tissue and/or generating temporary widening of the opening may be inserted through conduit 26 or otherwise deployed prior to insertion of the implant.

Figure 8:
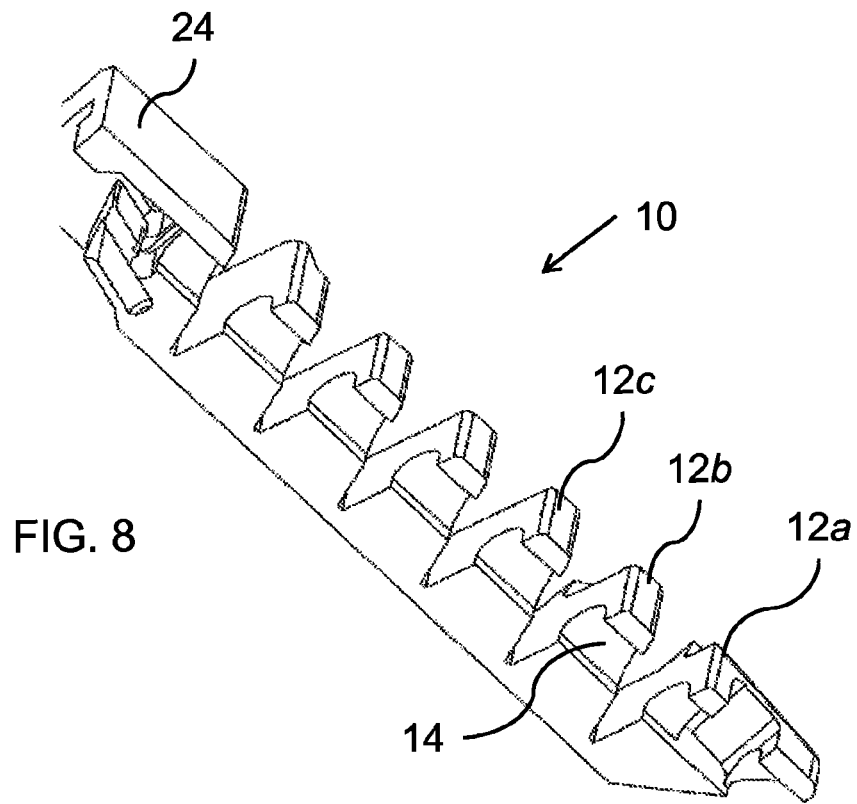
FIG. 8 is a schematic isometric cut-away view of an implant body according to a variant implementation of the present invention.
Figure 9:
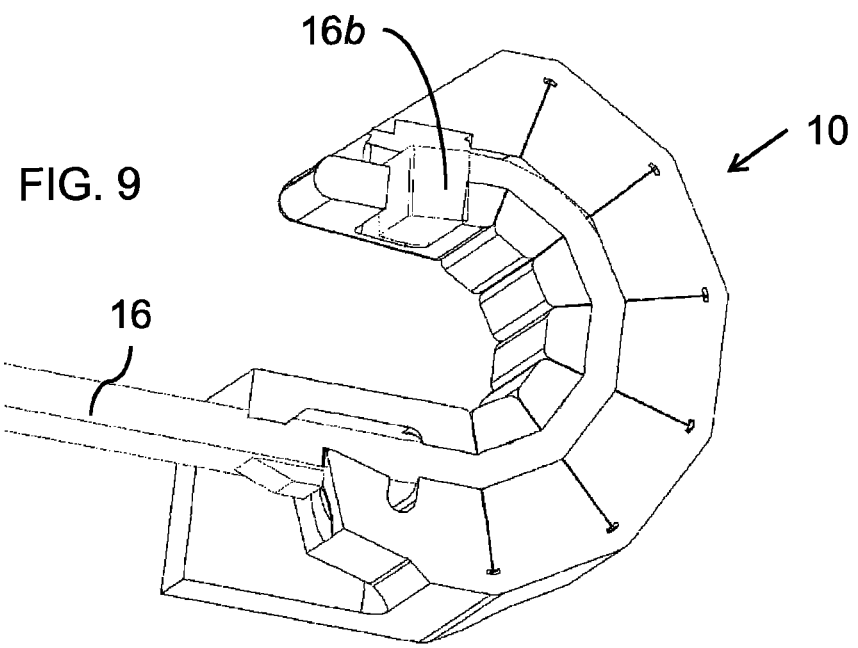
FIG. 9 is a schematic isometric cut-away view of the implant body of FIG. 8 together with a corresponding tightening element together forming an implant shown in its curved deployed state.
Figure 10:
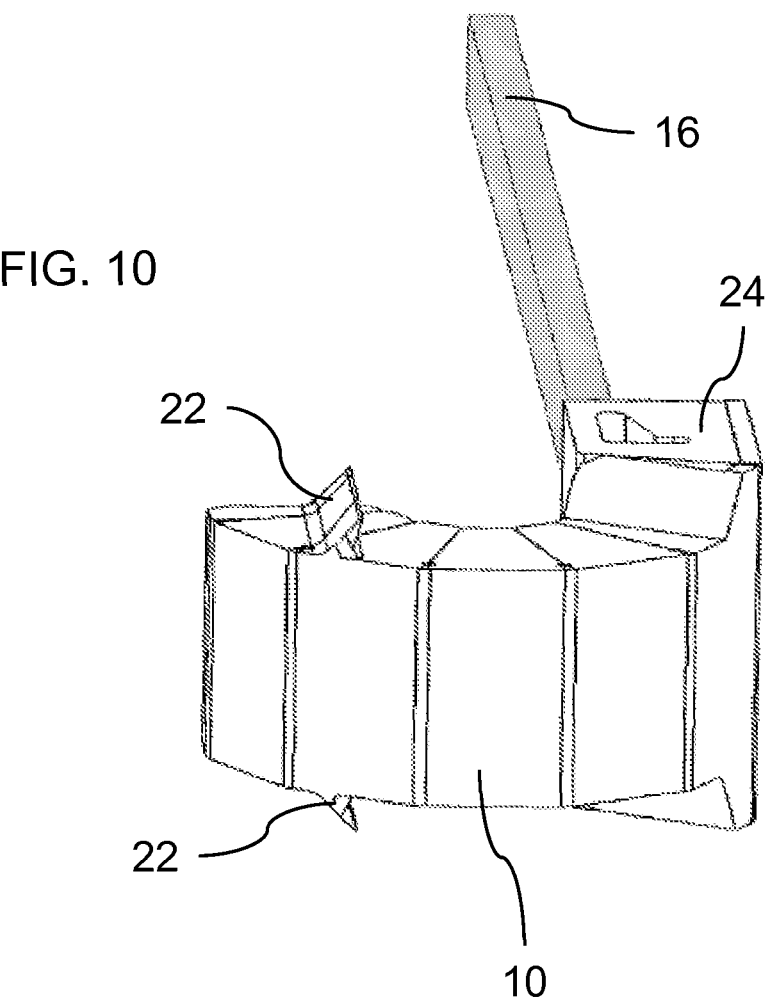
FIG. 10 is an anterior view of the implant of FIG. 9 in its curved deployed state.

Turning now to FIGS. 8-10, there is shown a variant implementation of the implant of the present invention. This variant is generally similar, but differs from the first implementation in the form of tightening element 16 and the manner in which it engages implant body 10.

Specifically, in the first implementation, tightening element 16 is integrally formed with a pointed tip portion 16a which forms the leading tip of the implant itself. In contrast, the implementation of FIGS. 8-10 employs an implant body 10 in which the distal segment 12a itself provides the distal tip of the implant. In this case, tightening element 16 is formed with a retaining block 16b which lodges within a recess of distal segment 12a at the beginning of channel 14.

In all other respects, the structure and function of the implementation of FIGS. 8-10 is analogous to that of the first implementation described above.

It will be appreciated that the above descriptions are intended only to serve as examples, and that many other embodiments are possible within the scope of the present invention as defined in the appended claims.

What is claimed is:

1. A spinal implant comprising:
   (a) an implant body including a plurality of segments hingedly interconnected so as to assume a straightened state for delivery along a conduit and a curved deployed state, said implant body having a channel passing from a distal one of said segments along a majority of a length of said body; and
   (b) an elongated tightening element anchored at said distal segment of said body and passing along said channel,
   said body and said tightening element being configured such that tension applied to said tightening element tends to bias said implant body from said straightened state to said curved deployed state,
   wherein said implant body and said tightening element are configured to provide a locking arrangement such that, when said tightening element is deflected to reach said curved deployed state, said locking arrangement is effective to lock said tightening element relative to said implant body, thereby retaining said implant in said curved deployed state,
   further comprising engagement features associated with said implant body and configured for engaging two adjacent spinous processes, wherein said implant body has a medial portion of a first width for deployment as a spacer between two adjacent spinous processes, and wherein said engagement features are associated with at least a proximal portion of said implant body and span a width greater than said first width so as to laterally engage the spinous processes, thereby limiting movement of said implant body relative to said spinous processes.

2. The implant of claim 1, wherein said implant body is formed with at least one resilient tooth, and wherein said tightening element is formed with at least one corresponding step, said resilient tooth and said corresponding step together providing said locking arrangement.

3. The implant of claim 1, wherein said curved deployed form exhibits a substantially U-shaped form.

4. The implant of claim 1, wherein said engagement features include a set of lateral projections formed at a distal portion of said implant body and configured for inhibiting withdrawal of said distal portion between adjacent regions of spinal tissue after deployment.

5. The implant of claim 4, wherein said lateral projections provide barbed ridges shaped to inhibit withdrawal of said distal portion between adjacent regions of spinal tissue after deployment.

6. The implant of claim 4, wherein said set of lateral projections includes projections from a plurality of said segments of said implant body, said projections being spaced apart when said implant body is in said straightened state and being juxtaposed when said implant is in said curved deployed state such that said projections cooperate to form at least one elongated retention feature extending along at least part of at least two of said segments.

7. The implant of claim 6, wherein said at least one elongated retention feature is a projecting ridge extending substantially perpendicular to a line joining a proximal and a distal end of said implant body.

8. The implant of claim 6, wherein said at least one elongated retention feature is a barbed ridge shaped to inhibit withdrawal of said distal portion between adjacent regions of spinal tissue after deployment.

9. The implant of claim 6, wherein said at least one elongated retention feature extends along at least part of at least three of said segments.

10. The implant of claim 4, wherein said engagement features further comprise a proximal block having a second width greater than said first width.

11. The implant of claim 1, wherein said implant body is formed primarily from a biocompatible polymer.

12. The implant of claim 1, wherein said implant body is formed primarily from ultra-high-molecular-weight poly-ethylene.

13. The implant of claim 12, wherein said tightening element is formed primarily from ultra-high-molecular-weight poly-ethylene.

14. An implant system comprising:
   (a) the implant of claim 1; and
   (b) a delivery system including:
      (i) a conduit sized to receive said implant and to maintain said implant body in said straightened state,
      (ii) a pusher deployable at least partially within said conduit to advance said implant so as to emerge from a distal opening of said conduit, and
      (iii) a biasing arrangement associated with said tightening element and deployed to urge said tightening element rearward such that, as said implant emerges from said distal end of said conduit, said implant body is progressively deflected towards said curved deployed state.

15. The implant system of claim 14, wherein said delivery system further includes a cutting mechanism selectively deployable to sever an excess length of said tightening element after locking of said locking arrangement.

16. A spinal implant comprising:
   (a) an implant body including a plurality of segments hingedly interconnected so as to assume a straightened state for delivery along a conduit and a curved deployed state, said implant body having a channel passing from a distal one of said segments along a majority of a length of said body;
   (b) an elongated tightening element anchored at said distal segment of said body and passing along said channel; and
   (c) engagement features associated with said implant body and configured for engaging two adjacent spinous processes,
   wherein said implant body has a medial portion of a first width for deployment as a spacer between two adjacent spinous processes, and wherein said engagement features are associated with a proximal portion and a distal portion of said implant body and span a width greater than said first width so as to laterally engage the spinous processes, thereby limiting movement of said implant body relative to said spinous processes,
   said body and said tightening element being configured such that tension applied to said tightening element tends to bias said implant body from said straightened state to said curved deployed state,
   wherein said engagement features include a set of lateral projections formed at a distal portion of said implant body and configured for inhibiting withdrawal of said distal portion between adjacent regions of spinal tissue after deployment.

17. The implant of claim 16, wherein said lateral projections provide barbed ridges shaped to inhibit withdrawal of said distal portion between adjacent regions of spinal tissue after deployment.

18. The implant of claim 16, wherein said set of lateral projections includes projections from a plurality of said segments of said implant body, said projections being spaced apart when said implant body is in said straightened state and being juxtaposed when said implant is in said curved deployed state such that said projections cooperate to form at least one elongated retention feature extending along at least part of at least two of said segments.

19. The implant of claim 18, wherein said at least one elongated retention feature is a projecting ridge extending substantially perpendicular to a line joining a proximal and a distal end of said implant body.

20. The implant of claim 18, wherein said at least one elongated retention feature is a barbed ridge shaped to inhibit withdrawal of said distal portion between adjacent regions of spinal tissue after deployment.

21. The implant of claim 18, wherein said at least one elongated retention feature extends along at least part of at least three of said segments.

22. The implant of claim 16, wherein said engagement features further comprise a proximal block having a second width greater than said first width.

23. The implant of claim 16, wherein said curved deployed form exhibits a substantially U-shaped form.

24. A spinal implant comprising:
   (a) an implant body including a plurality of segments hingedly interconnected so as to assume a straightened state for introduction into a body and a curved deployed state; and
   (b) engagement features associated with said implant body and configured for engaging two adjacent spinous processes, wherein said implant body has a medial portion of a first width for deployment as a spacer between two adjacent spinous processes, and wherein said engagement features are associated with at least a proximal portion of said implant body and span a width greater than said first width so as to laterally engage the spinous processes, thereby limiting movement of said implant body relative to the adjacent spinous processes.

* * * * *